United States Patent [19]
Edwards

[11] Patent Number: 5,743,904
[45] Date of Patent: Apr. 28, 1998

[54] PRECISION PLACEMENT OF ABLATION APPARATUS

[75] Inventor: Stuart D. Edwards, Portola Valley, Calif.

[73] Assignee: Somnus Medical Technologies, Inc., Sunnyvale, Calif.

[21] Appl. No.: 660,539

[22] Filed: Jun. 7, 1996

Related U.S. Application Data

[63] Continuation-in-part of Ser. No. 651,800, May 22, 1996, and Ser. No. 651,378, May 22, 1996, and Ser. No. 643,203, May 6, 1996, Pat. No. 5,718,702, and Ser. No. 643,524, May 6, 1996, and Ser. No. 651,796, May 22, 1996, and Ser. No. 651,798, May 22, 1996.

[51] Int. Cl.$^6$ ............................................. A61B 17/36
[52] U.S. Cl. ............................................. 606/32; 607/134
[58] Field of Search ................ 606/27–50; 607/96–101, 607/119, 122, 134

[56] References Cited

U.S. PATENT DOCUMENTS

| | | | |
|---|---|---|---|
| 3,901,241 | 8/1975 | Allen | 128/303.1 |
| 4,011,872 | 3/1977 | Komiya | 128/303.14 |
| 4,411,266 | 10/1983 | Cosman | 128/303.18 |
| 4,423,812 | 1/1984 | Sato | 206/387 |

(List continued on next page.)

FOREIGN PATENT DOCUMENTS

| | | |
|---|---|---|
| WO 92/10142 | 6/1992 | WIPO. |
| WO 93/08755 | 5/1993 | WIPO. |
| 94 10925 A | 5/1994 | WIPO. |
| 95 18575 A | 7/1995 | WIPO. |
| WO 96/29946 | 10/1996 | WIPO. |

OTHER PUBLICATIONS

Kaneko, et al., *Physiological Laryngeal Pacemaker*, May 1985, Trans Am Soc Artif Intern Organs, vol. XXXI, pp. 293–296.

Mugica, et al., *Direct Diaphragm Stimulation*, Jan. 1987, PACE, vol. 10, pp. 252–256.

Mugica, et al., *Neurostimulation: An Overview*, Chapter 21, Preliminary Test of a Muscular Diaphragm Pacing System on Human Patients, 1985, pp. 263–279.

Nochomovitz, et al., *Electrical Activation of the Diaphragm*, Jun. 1988, Clinics in Chest Medicine, vol. 9, No. 2, pp. 349–358.

Prior, et al., *Treatment of Menorrhagia by Radiofrequency Heating*, 1991, Int. J. Hyperthermia, vol. 7, pp. 213–220.

Rice, et al., *Endoscopic Paranasal Sinus Surgery*, Chapters 5, Functional Endoscopic Paranasal Sinus Surgery, The Technique of Messerklinger, Raven Press, 1988, pp. 75–104.

Rice, et al., *Endoscopic Paranasal Sinus Surgery*, Chapters 6, Total Endoscopic Sphenoethmoidectomy, The Technique of Wigand, Raven Press, 1988, pp. 105–125.

*Primary Examiner*—Jeffrey R. Jastrzab
*Attorney, Agent, or Firm*—Wilson Sonsini Goodrich & Rosati

[57] ABSTRACT

The invention provides a method and system for precision placement of ablation apparatus. An ablation catheter having a plurality of electrodes and having a radius of curvature selected responsive to a size of a patient's tongue, is placed near to the tongue and offset from a gag-response region in the throat, preferably using an optical viewing apparatus and a view port in the catheter. The ablation catheter is coupled to a baseplate and to a measuring device for indicating an offset of a selected reference point of the ablation catheter from the baseplate. The baseplate is coupled to a reference body structure, such as the jaw, lips or teeth. In cases where multiple ablation operations are conducted, the ablation catheter (or a replacement ablation catheter) is coupled to the baseplate so that the selected reference point has the same distance from the baseplate, and thus from the reference body structure. The reference body structure is a selected region of the lips and teeth, and the baseplate is coupled thereto by filling that region with a dental cement or other quick-setting compound, so as to create a dental fixture which is fitted to the patient.

6 Claims, 2 Drawing Sheets

U.S. PATENT DOCUMENTS

| Patent # | Date | Inventor | Class |
|---|---|---|---|
| 4,532,924 | 8/1985 | Auth et al. | 128/303.17 |
| 4,565,200 | 1/1986 | Cosman | 128/642 |
| 4,901,737 | 2/1990 | Toone | 128/848 |
| 4,906,203 | 3/1990 | Margrave et al. | 439/188 |
| 4,907,589 | 3/1990 | Cosman | 606/34 |
| 4,947,842 | 8/1990 | Marchosky et al. | 128/401 |
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |
| 5,100,423 | 3/1992 | Fearnot | 606/159 |
| 5,122,137 | 6/1992 | Lennox | 606/40 |
| 5,125,928 | 6/1992 | Parins et al. | 606/48 |
| 5,190,541 | 3/1993 | Abele et al. | 606/46 |
| 5,197,963 | 3/1993 | Parins | 606/46 |
| 5,197,964 | 3/1993 | Parins | 606/48 |
| 5,215,103 | 6/1993 | Desai | 128/784 |
| 5,239,982 | 8/1993 | Trauthen | 600/117 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,324,288 | 6/1994 | Billings et al. | 606/32 |
| 5,328,467 | 7/1994 | Edwards et al. | 604/95 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,366,490 | 11/1994 | Edwards et al. | 607/99 |
| 5,368,592 | 11/1994 | Stern et al. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,403,311 | 4/1995 | Abele et al. | 606/49 |
| 5,409,453 | 4/1995 | Lundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,433,739 | 7/1995 | Sluijter et al. | 607/99 |
| 5,435,805 | 7/1995 | Edwards et al. | 604/22 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,464,404 | 11/1995 | Abela et al. | 606/15 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 | 1/1996 | Edwards et al. | 604/22 |
| 5,486,161 | 1/1996 | Lax et al. | 604/22 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |

PRECISION PLACEMENT OF ABLATION APPARATUS

CROSS-REFERENCE TO RELATED APPLICATIONS

This application is a continuation-in-part of the following co-pending applications: application Ser. No. Express Mail mailing application Ser. No. 08/651,800, filed May 22, 1996; application Ser. No. 08/651,378, filed May 22, 1996; application Ser. No. 08/643,203, filed May 6, 1996 now U.S. Pat. No. 5,718,702; application Ser. No. 08/643,524, filed May 6, 1996; application Ser. No. 08/651,796, filed May 22, 1996; and application Ser. No. 08/651,798, filed May 22, 1996; each of which are incorporated herein by reference.

BACKGROUND OF THE INVENTION

1. Field of the Invention

This invention relates to precision placement of ablation apparatus.

2. Description of Related Art

In ablating tissue or other body structures, ablation apparatus is either inserted into tissue inside the body, such as with the aid of devices for seeing inside body structures (such as a fluoroscope, x-ray device, or related device), or is inserted into tissue accessible from outside the body and directly viewable therefrom.

One problem in the art is that present methods of placement for ablation apparatus are unsuited for ablating tissue in the tongue and other regions near the ear, nose or throat. Some examples of such other regions are the uvula, soft palette, tonsils, adenoids, laryngeal tissues, and fatty tissues in the cheeks, jaw, and near the eyes. Subjecting these regions to fluoroscopy or similar techniques has the disadvantage that the patient could be overexposed to x-rays or other radiation.

Another problem with ablating tissue in the tongue and other regions near the ear, nose or throat, is that it may be necessary to conduct multiple operations in which tissue is ablated. In those cases, it would be advantageous to place ablation apparatus in the identical location, relative to the body structure to be ablated, for each of the multiple operations.

Accordingly, it would be advantageous to provide a technique for precision placement of ablation apparatus, particularly for ablation apparatus used for the tongue and other regions near the ear, nose and throat.

SUMMARY OF THE INVENTION

The invention provides a method and system for precision placement of ablation apparatus. An ablation catheter having a plurality of electrodes and having a radius of curvature selected responsive to a size of a patient's tongue, is placed near to the tongue and offset from a gag-response region in the throat, preferably using an optical viewing apparatus and a view port in the catheter. The ablation catheter is coupled to a baseplate and to a measuring device for indicating an offset of a selected reference point of the ablation catheter from the baseplate. The baseplate is coupled to a reference body structure, such as the jaw, lips or teeth. In cases where multiple ablation operations are conducted, the ablation catheter (or a replacement ablation catheter) is coupled to the baseplate so that the selected reference point has the same distance from the baseplate, and thus from the reference body structure.

In a preferred embodiment, the reference body structure is a selected region of the lips and teeth, and the baseplate is coupled thereto by filling that region with a dental cement or other quick-setting compound, so as to create a dental fixture which is fitted to the patient.

DESCRIPTION OF THE PREFERRED EMBODIMENT

Figure 1A:
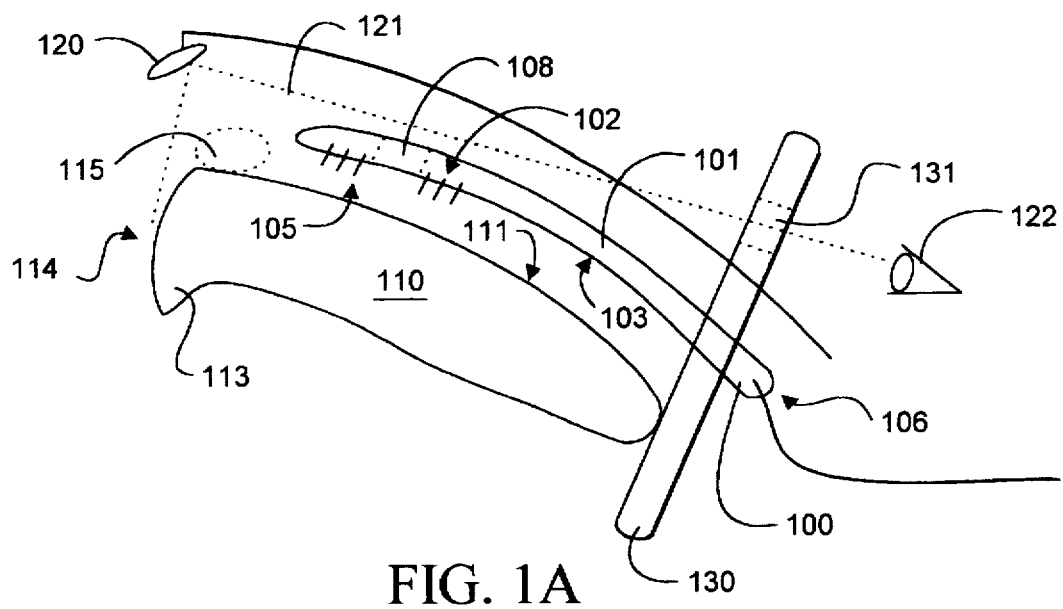
FIG. 1A shows a first view of apparatus for precision placement of ablation apparatus.
Figure 1B:
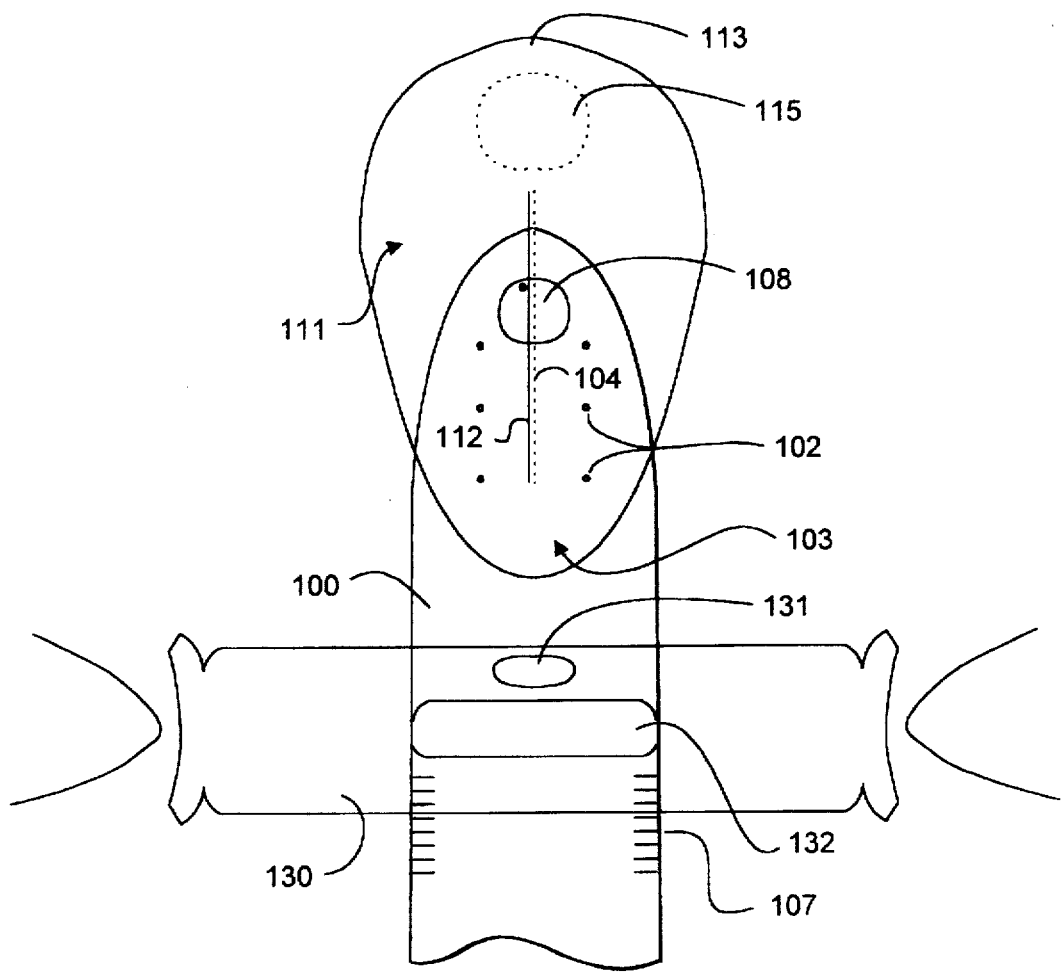
FIG. 1B shows a second view of apparatus for precision placement of ablation apparatus.
Figure 1C:
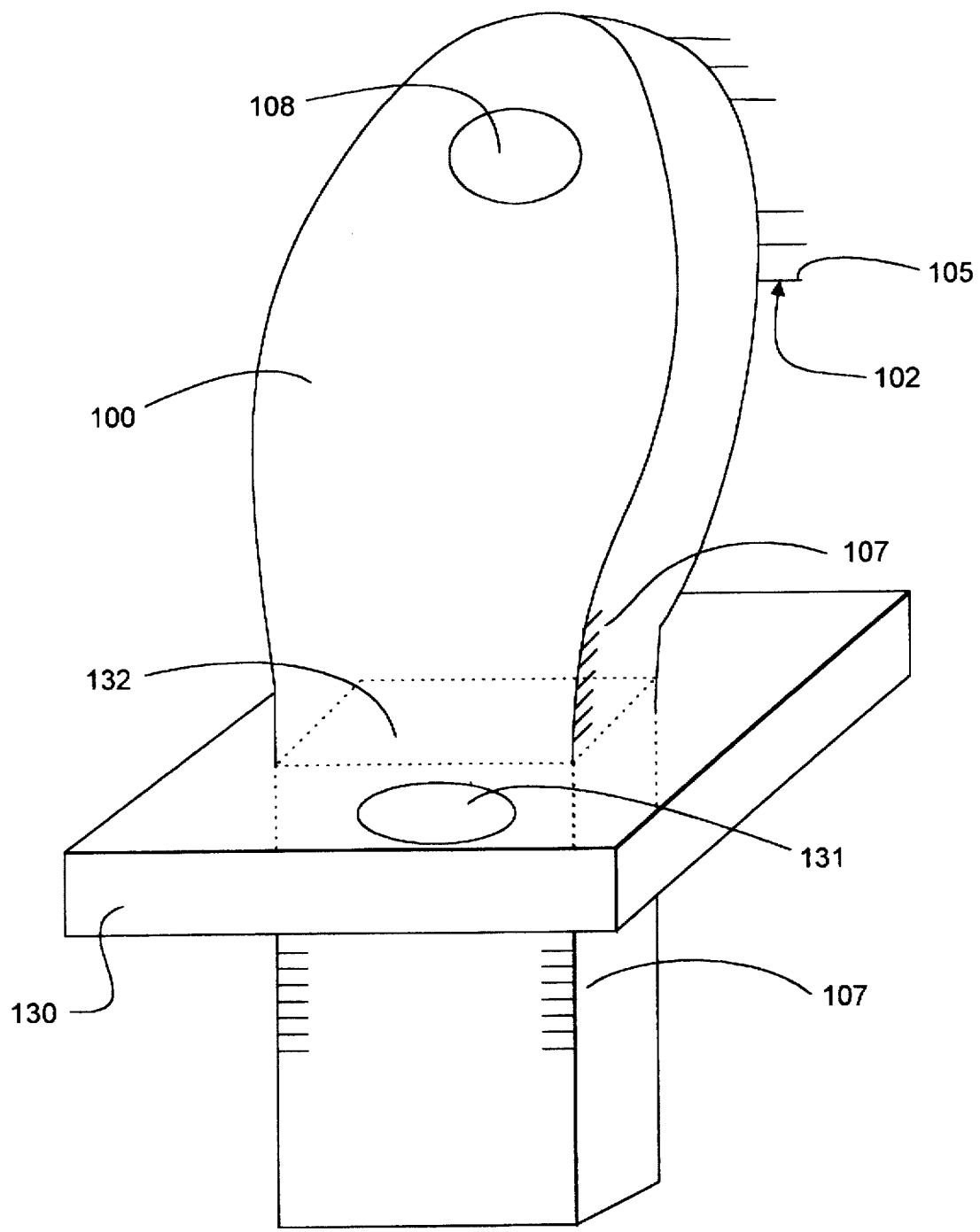
FIG. 1C shows a third view of apparatus for precision placement of ablation apparatus.

FIG. 1A shows a first view, FIG. 1B shows a second and FIG. 1C shows a third view, of apparatus for view, precision placement of ablation apparatus.

An ablation catheter 100 is placed near to a patient's tongue 110 and disposed for ablating at least a portion of the tongue 110. In a preferred embodiment, the ablation catheter 100 comprises a curved element 101 and a plurality of electrodes 102 coupled thereto. Each electrode 102 is coupled to the curved element 101 at an angle between about 20 degrees and about 30 degrees from a right angle, although another angle would also be workable. The electrodes 102 are disposed for delivering an ablative agent, preferably RF energy but possibly another ablative agent such as an ablative chemical, to the tongue 110.

The curved element 101 comprises a relatively broad and flat surface 103 and is disposed over a relatively broad and flat surface 111 of the tongue 110, with a lengthwise axis 104 of the curved element 101 substantially aligned with a lengthwise axis 112 of the tongue 110. In a preferred embodiment, the curved element 101 has a radius of curvature which is selectable in response to a radius of curvature, or a size and shape, of the tongue 110.

The electrodes 102 are disposed in pairs, each pair being disposed about the lengthwise axis 104 of the curved element 101 and each being offset therefrom by about 1 centimeter, and each pair being offset from adjacent pairs by about 2 centimeters. An odd electrode 102 is disposed on the lengthwise axis 104.

The electrodes 102 comprise relatively sharp tips 105 for insertion into the tongue 110 and are disposed so as to be inserted with said tips 105 a substantial depth below the surface 111 of the tongue 110. The electrodes 102 are disposed so as to be retractable into the body of the curved element 101. In a preferred embodiment, the electrodes 102 are disposed in a selected pattern, with each electrode 102 having a selected position on the surface of the curved element 101 and having a selected length, so as to achieve a selected three-dimensional ("3D") pattern of said tips 105 within the tongue 110 when said curved element 101 is brought near to or in contact with the tongue 110.

Each electrode 102 is coupled to a tube or another mechanism in the ablation catheter 100 for delivering saline or other substances to the electrode 102. The ablation catheter 100 is therefore coupled at a rear position 106 to tubing or another mechanism for delivering saline or other substances to the electrodes 102.

The tongue 110 comprises a chevron 113 at a base end 114 of the tongue 110. A gag-response region 115 is located near to the chevron 113, and is defined by the property that if objects of any substantial size are placed therein, the patient is likely to have a gag response.

A mirror 120 is disposed near the chevron 113 (and outside the gag-response region 115), so as to present a line of sight 121 between the chevron 113 and a viewing location 122 substantially outside the patient's mouth. In a preferred embodiment, the mirror 120 is held by a handle, but in alternative embodiments, the mirror 120 may be coupled to the ablation catheter 100 or some other structure. A viewing window 108 disposed through the catheter 100 allows the line of sight 121 to pass through the catheter 100. In a preferred embodiment, the viewing window 108 comprises a clear substance disposed in the curved element 101, such as a clear plastic, but in alternative embodiments, the viewing window 108 may comprise a hole in the curved element 101, a translucent substance disposed in the curved element 101, or another type of optical pathway, such as an optical fiber.

Medical personnel are thereby able to view the position of the ablation catheter 100 relative to the chevron 113, so as to position the ablation catheter 100 relative to the chevron 113 (and outside the gag-response region 115). In alternative embodiments, alternative devices could be used for viewing in place the mirror 120, such as a light path comprising optical fiber, a small camera, or another technique.

A base plate 130 is disposed at the entrance to the patient's mouth and coupled to a portion of the patient's jaw, lips or teeth. The base plate 130 is temporarily affixed to the patient's teeth using dental cement. In a preferred embodiment, the dental cement fills the mouth opening, so as to create a mold which prevents the passage of air into and out of the patient's mouth through the lips (but still allowing the patient to breathe through the nose).

In a preferred embodiment where a mirror 120 is used for viewing the tongue 110 and its chevron 113, the base plate comprises a window 131 which is positioned so the line of sight 121 is not blocked. The window 131 comprises a clear pane such as clear plastic or glass.

The base plate 130 is shaped to define a slot 132 through which the ablation catheter 100 may slide into and out of the patient's mouth. By sliding the ablation catheter 1 00 into and out of the patient's mouth, the ablation catheter 100 is disposed respectively relatively further in and closer to the chevron 113 or relatively further out and farther away from the chevron 113.

The ablation catheter 100 (or a handle or other element coupled thereto) is labeled with a set of markings which serve as a position indicator 107. Thereby, when the ablation catheter 100 is moved, the position indicator 107 shows a new value for the relative position of the ablation catheter 100 and the base plate 130 by virtue of the marking which is next to the base plate 130.

In alternative embodiments, other types of position indicator 107 may be coupled to the ablation catheter 100; for example, the position indicator 107 may comprise a wheeled sensor, an inductive sensor, or another type of sensor which is sensitive to movement of the ablation catheter 100. Moreover, other types of display of the indicated position may be used; for example, the position indicator 107 may comprise a digital or other numerical readout.

The ablation catheter 100 has a radius of curvature which is adjustable. In a preferred embodiment, the position indicator 107 also indicates that radius of curvature, as well as any other adjustable features of the ablation catheter 100, as those adjustments are made. For example, other adjustable features of the ablation catheter 100 may comprise angles for placement relative to a long axis and a horizontal cross axis of the ablation catheter 100.

In a preferred embodiment, multiple operations are performed to ablate the tongue 110, using a process such as the following.

In a preferred embodiment, the first such operation comprises the following steps:

1. The base plate 130 is temporarily affixed to the patient's teeth using dental cement; a mold is created which prevents the passage of air into and out of the patient's mouth through the lips.

2. The patient's mouth is disinfected using a known disinfectant.

3. The ablation catheter 100 is positioned to ablate at least a portion of the tongue 110.

4. The position indicator 107 thereby indicates a position of the ablation catheter 100 relative to the base plate 130. The indicated position is recorded, such as by reading the indicated position value and writing that value on a patient's chart or other record.

5. The ablation catheter 100 is used to ablate at least a portion of the tongue 110 in a first such operation.

6. The ablation catheter 100 is removed from the patient's mouth and from the base plate 130.

7. The base plate 130 is removed from the patient's mouth and stored for a second such operation.

In a preferred embodiment, the second such operation comprises the following steps:

1. The base plate 130 and mold are temporarily re-affixed to the patient's teeth using dental cement.

2. The patient's mouth is disinfected using a known disinfectant.

3. An ablation catheter 100 (this may comprise a new ablation catheter 100, an old ablation catheter 100 which has been sterilized, or an old ablation catheter 100 which has been sterilized and fitted with replacement electrodes 102) is positioned to ablate at least a portion of the tongue 110.

4. The recorded position is read from the patient's chart or other record.

5. The ablation catheter 100 is moved and otherwise adjusted until the position indicator 107 thereby indicates the same position and other adjustment of the ablation catheter 100 relative to the base plate 130 as for the first such operation.

6. The ablation catheter 100 is used to ablate at least a portion of the tongue 110 in a second such operation.

7. The ablation catheter 100 is removed from the patient's mouth and from the base plate 130.

8. The base plate 130 is removed from the patient's mouth and stored for any further such operations.

In certain cases, it may be necessary to alter the values indicated by the position indicator 107 for the second and subsequent such operations, such as for example to adjust to shrinkage of the tongue 110 or to adjust for patient growth if the patient is a child.

Alternative Embodiments

Although the invention has been described with reference to preferred embodiments, it would be clear to those skilled in the art that alternative embodiments exist and are within the scope and spirit of the invention.

For example, although the invention is described herein for use with the tongue, it would be clear to those skilled in the art, after perusal of this application, that the invention is also applicable to other body structures, such as the uvula, soft palette, tonsils, adenoids, laryngeal tissues, and fatty tissues in the cheeks, jaw, and near the eyes.

The invention claimed is:

1. A system for positioning a distal end of an ablation catheter at a desired position within an oral cavity of a patient comprising:

a baseplate shaped to be immobilized relative to teeth of the patient, the baseplate including a slot through which the catheter can be introduced into the oral cavity;

an ablation catheter inserted passed through the slot adapted to be passed into the oral cavity; and a position indicator for indicating the position of the catheter distal end within the oral cavity based on a relative position of the catheter distal end to the baseplate.

2. The system according to claim 1 wherein the system further includes a composition which in combination with the baseplate forms a dental fixture molded to the patient's teeth.

3. The apparatus according to claim 1 wherein the position indicator is attached to the baseplate.

4. The apparatus according to claim 1 wherein the position indicator is attached to the catheter.

5. The apparatus according to claim 1 wherein the baseplate further includes a window through which an optical view of the oral cavity can be obtained.

6. A method for positioning a distal end of an ablation catheter at a desired position within an oral cavity of a patient comprising:

introducing a baseplate shaped to be immobilized relative to teeth of the patient into the oral cavity, the baseplate including a slot through which the ablation catheter can be introduced into the oral cavity;

adding a composition to the baseplate to form a dental fixture molded to the patient's teeth; and introducing a distal end of the ablation catheter through the slot into the oral cavity, one of the baseplate and catheter including a position indicator which indicates the position of the ablation catheter distal end within the oral cavity based on a relative position of the catheter distal end to the baseplate.

* * * * *